(12) United States Patent
Bern

(10) Patent No.: US 12,394,946 B2
(45) Date of Patent: Aug. 19, 2025

(54) MEDICAL SYSTEM WITH CONNECTOR FORMING AN EXTERNAL WINDING

(71) Applicant: InvivoPower AB, Mölndal (SE)

(72) Inventor: Bengt Bern, Mölndal (SE)

(73) Assignee: InvivoPower AB, Molndal (SE)

( * ) Notice: Subject to any disclaimer, the term of this patent is extended or adjusted under 35 U.S.C. 154(b) by 497 days.

(21) Appl. No.: 17/762,943

(22) PCT Filed: Oct. 27, 2020

(86) PCT No.: PCT/SE2020/051039
§ 371 (c)(1),
(2) Date: Mar. 23, 2022

(87) PCT Pub. No.: WO2021/091454
PCT Pub. Date: May 14, 2021

(65) Prior Publication Data
US 2022/0360024 A1 Nov. 10, 2022

(30) Foreign Application Priority Data
Nov. 7, 2019 (SE) .................... 1951275-5

(51) Int. Cl.
*H01R 13/66* (2006.01)
*A61B 17/12* (2006.01)

(52) U.S. Cl.
CPC ......... *H01R 13/66* (2013.01); *A61B 17/1214* (2013.01)

(58) Field of Classification Search
CPC ............... H01R 13/66; A61B 17/1214; A61B 2560/0219; A61M 2205/82; H02J 2310/23; A61N 1/3787
See application file for complete search history.

(56) References Cited

U.S. PATENT DOCUMENTS

| 6,032,076 A | 2/2000 | Melvin et al. |
| 10,692,642 B2 | 6/2020 | Ridler et al. |

(Continued)

FOREIGN PATENT DOCUMENTS

WO 2017072674 A1 5/2017

OTHER PUBLICATIONS

Swedish International Search Report and Written Opinion for International Application No. PCT/SE2020/051039, dated Dec. 28, 2020, 11 pages.

(Continued)

*Primary Examiner* — Carl H Layno
*Assistant Examiner* — Aya Ziad Bakkar
(74) *Attorney, Agent, or Firm* — Westman, Champlin & Koehler, P.A.

(57) ABSTRACT

A medical system comprising an internal unit; a transformer core; internal cabling comprising an internal winding around the transformer core; and an external unit comprising power supply circuitry and external cabling coupled to the power supply circuitry for enabling supply of power from the power supply circuitry to the internal unit via the transformer core. The external cabling comprises a connector including a first connector part and a second connector part; a first conductive current path between the power supply circuitry and the first connector part; a second conductive current path between the power supply circuitry and the second connector part; and a third conductive current path between the first connector part and the second connector part, conductively connecting the first connector part and the second connector part.

8 Claims, 13 Drawing Sheets

(56) References Cited

U.S. PATENT DOCUMENTS

| | | | |
|---|---|---|---|
| 11,348,720 B2 | 5/2022 | Ridler et al. | |
| 2006/0259096 A1* | 11/2006 | Ayre | A61M 60/873 |
| | | | 607/60 |
| 2010/0106225 A1 | 4/2010 | Ayre et al. | |
| 2014/0176063 A1* | 6/2014 | Forsell | H02J 50/80 |
| | | | 320/108 |
| 2017/0117086 A1 | 4/2017 | Ridler et al. | |
| 2019/0051988 A1* | 2/2019 | Bern | A61N 1/0529 |
| 2020/0395168 A1 | 12/2020 | Ridler et al. | |
| 2022/0293330 A1 | 9/2022 | Ridler et al. | |

OTHER PUBLICATIONS

Andren et al., "The Skin Tunnel Transformer: A New System that Permits Both High Efficiency Transfer of Power and Telemetry of Data Through the Intact Skin", IEEE Transactions on Biomedical Engineering, Oct. 1, 1968, vol. BME-15, No. 4, p. 278-280.

Topaz, "The Skin Tunnel Transformer as a Transcutaneous Electrical Coupling", IEEE Transactions on Magnetics, Jun. 1, 1970, vol. 6, No. 2, p. 332-334.

Shiba et al., "Analysis of specific absorption rate in biological tissue surrounding transcutaneous transformer for an artificial heart", Journal of Artificial Organs, 2002, vol. 5, No. 2, p. 91-96.

McArthur et al., "A new inexpensive cardiac pacing system", Singapore Medical Journal, Sep. 1973, vol. 14, No. 3, p. 435-438.

Shibuya et al., "Externally-Coupled Transcutaneous Energy Transmission for a Ventricular Assist Device-Miniaturization of Ferrite Core and Evaluation of Biological Effects around the Transformer", IEEE Biomedical Circuits and Systems Conference, Oct. 31, 2013, p. 206-209.

Extended European Search Report, for corresponding European Patent Application No. 20885774.8, dated Jul. 24, 2023, 7 pages.

\* cited by examiner

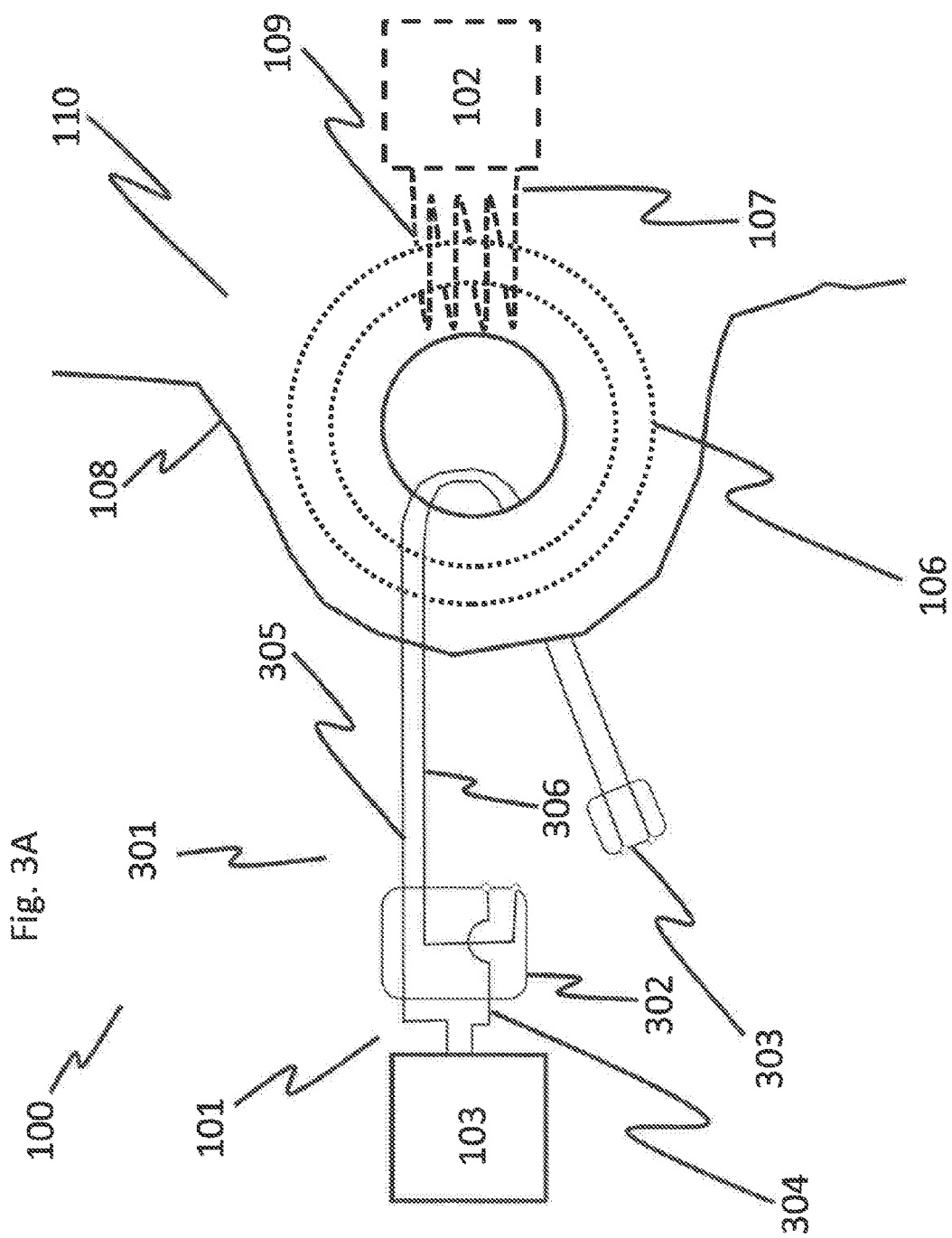

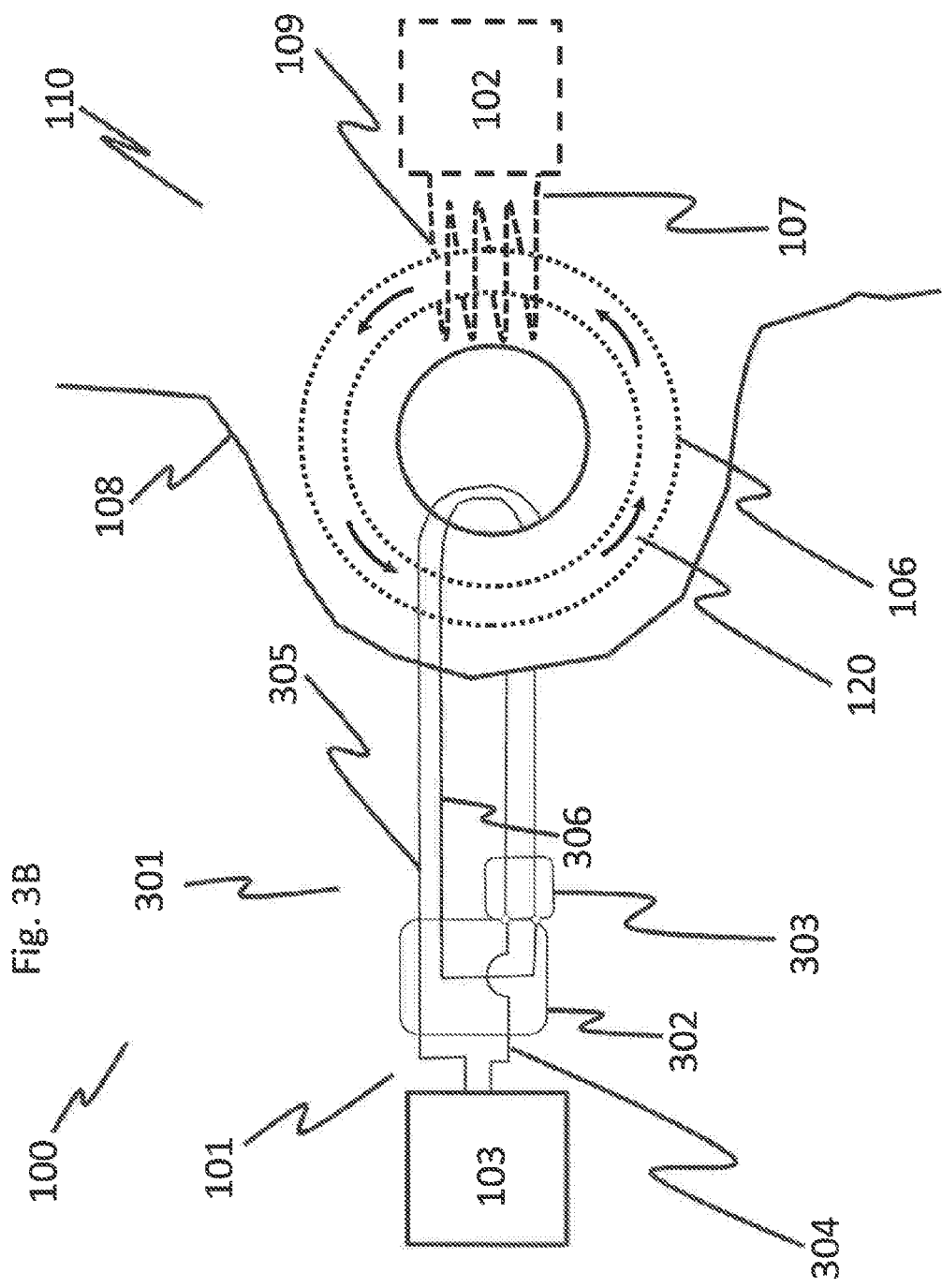

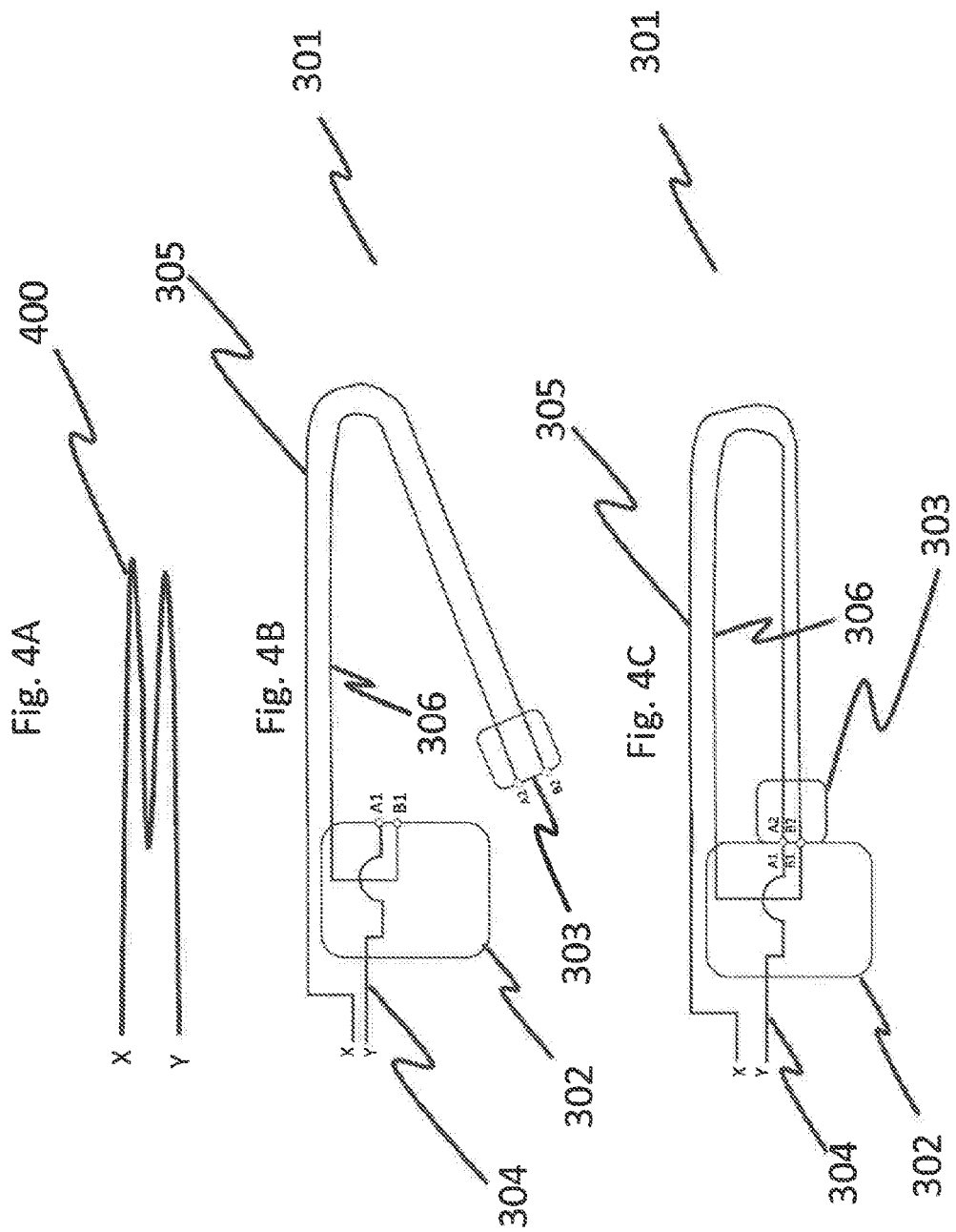

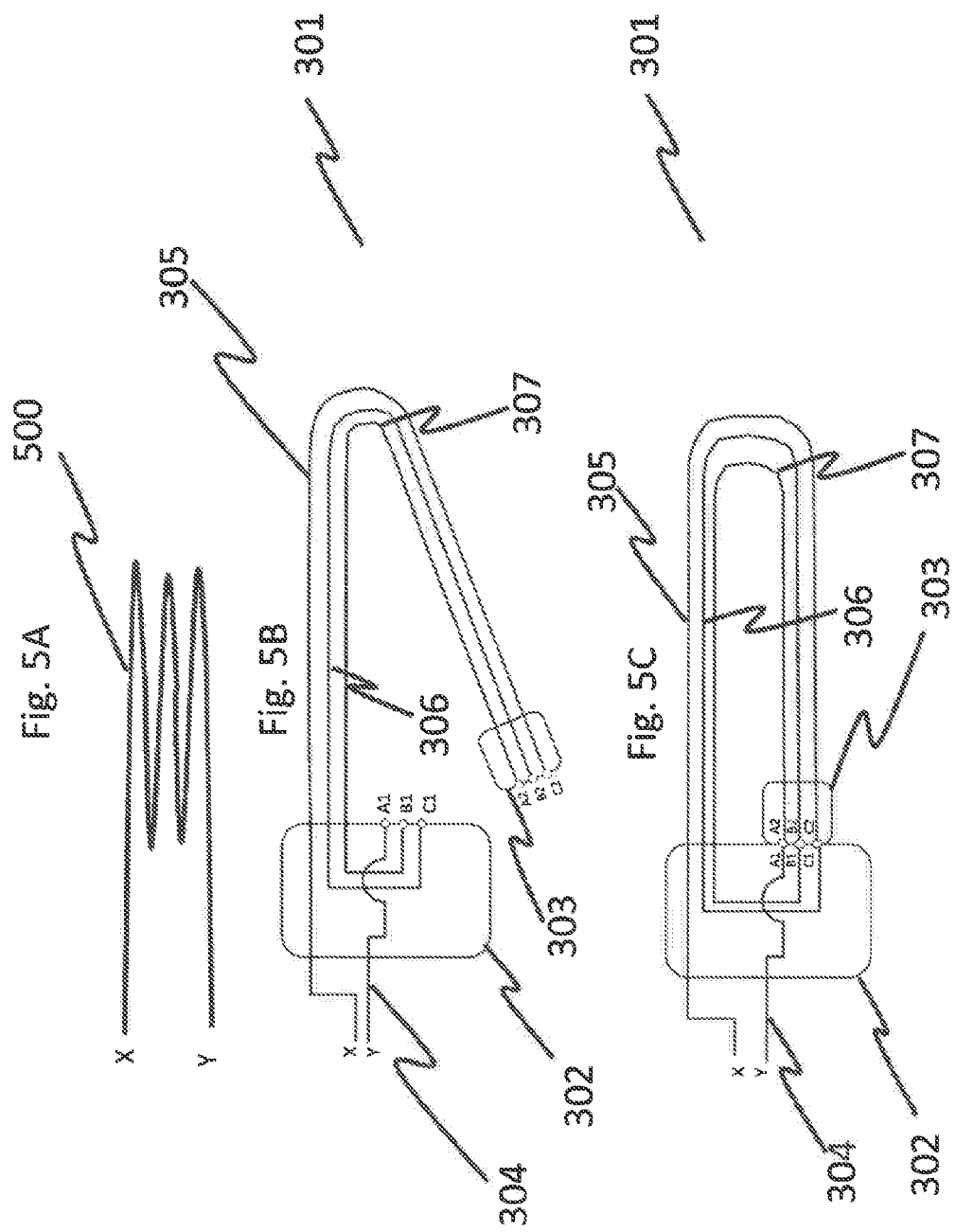

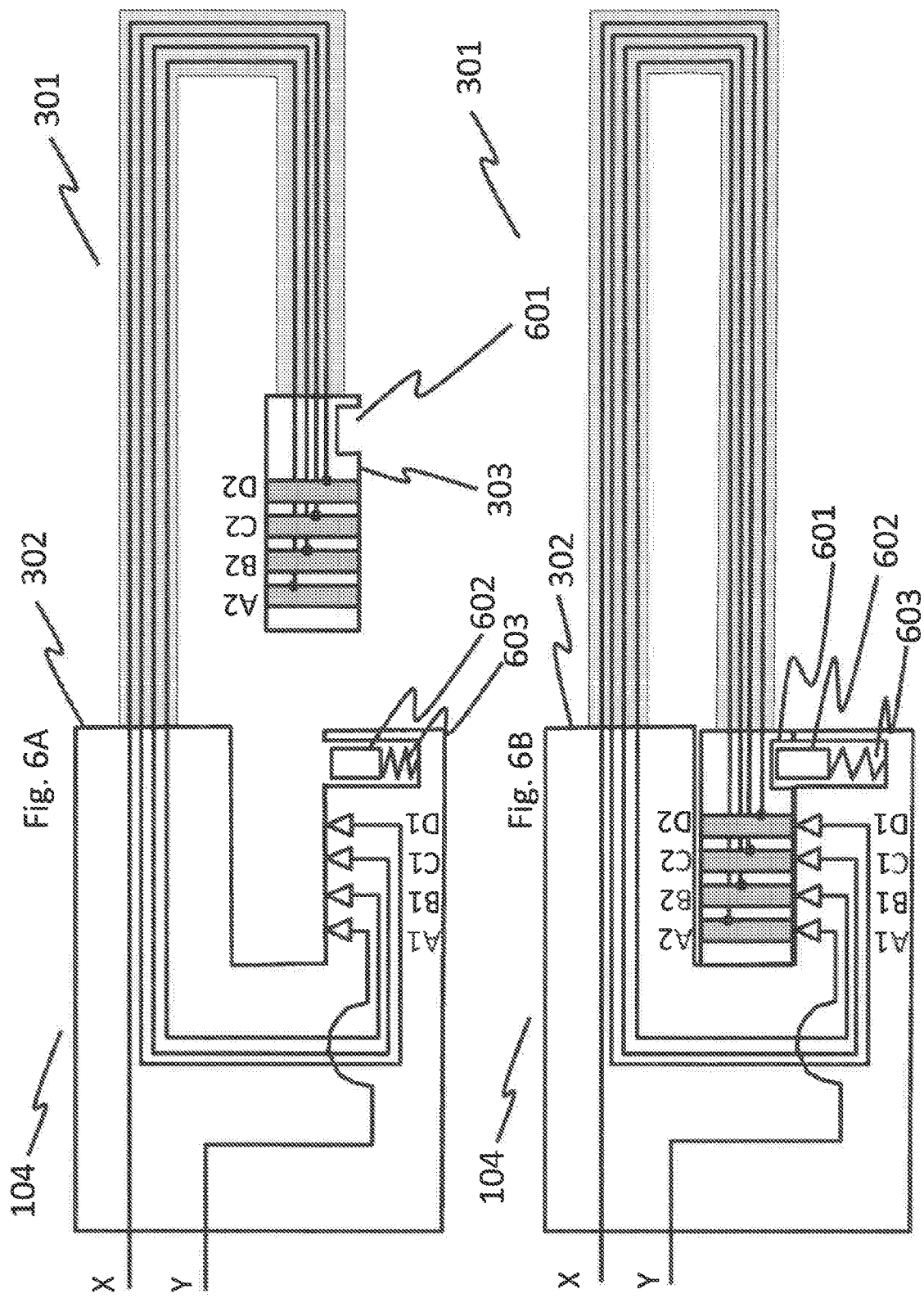

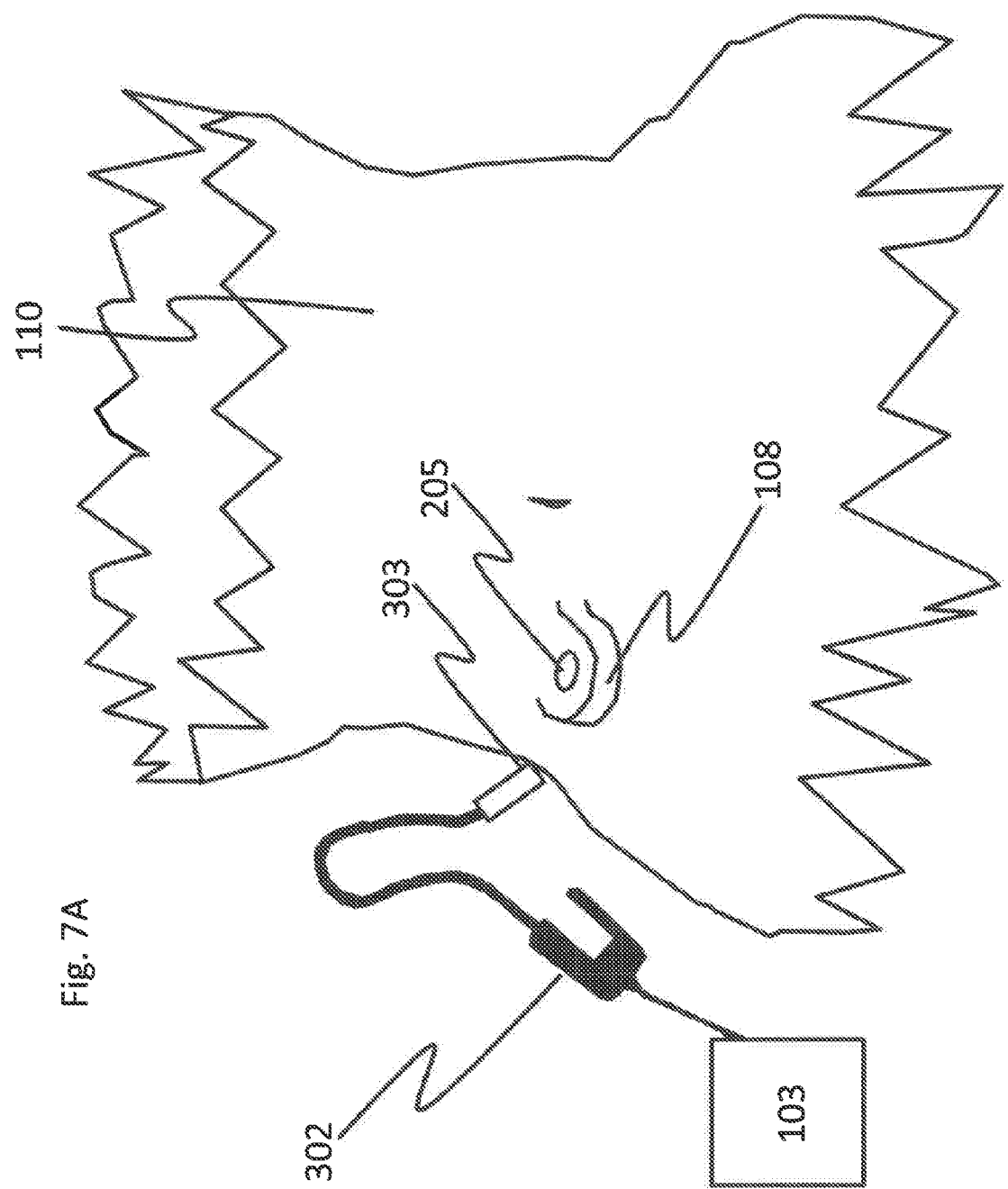

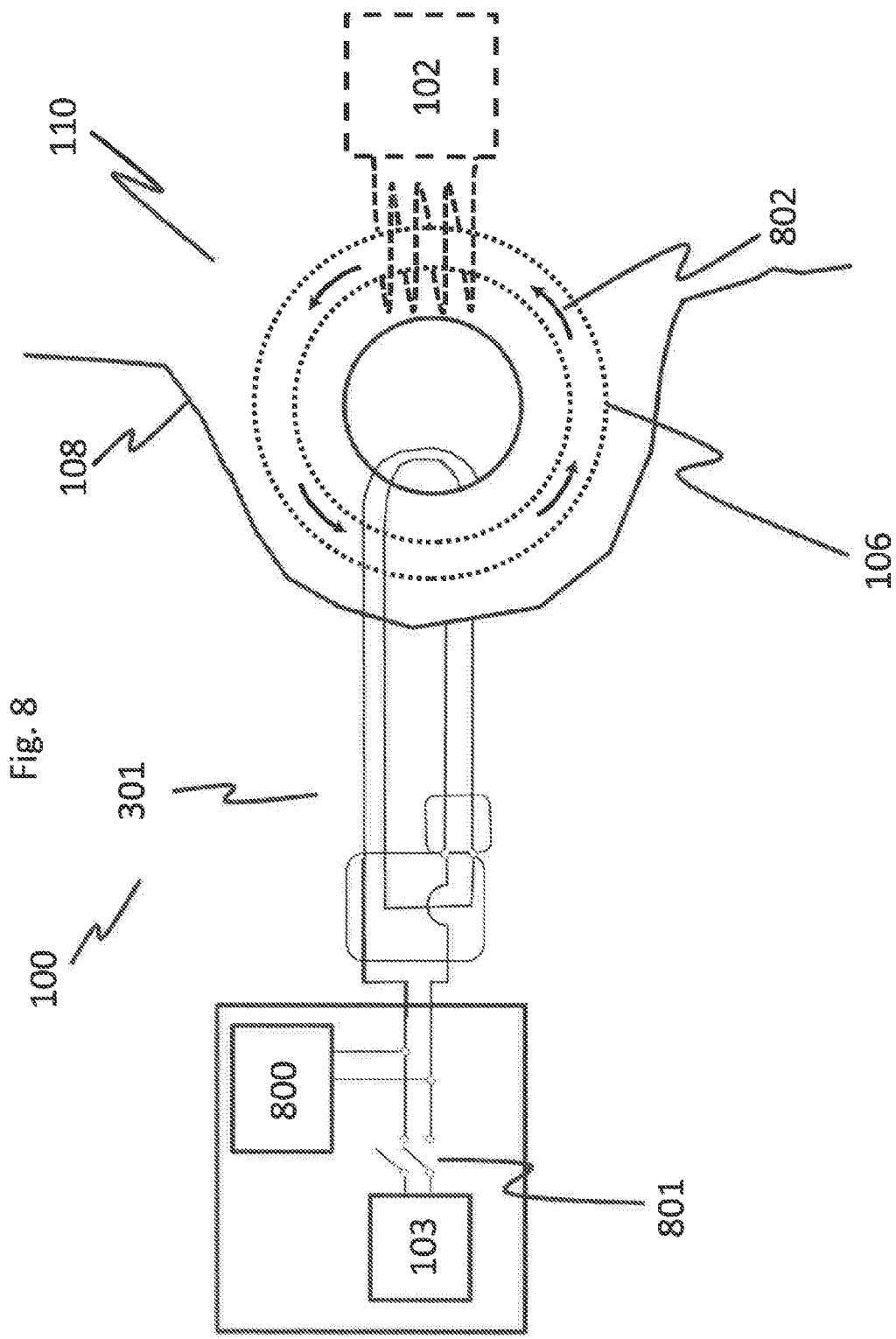

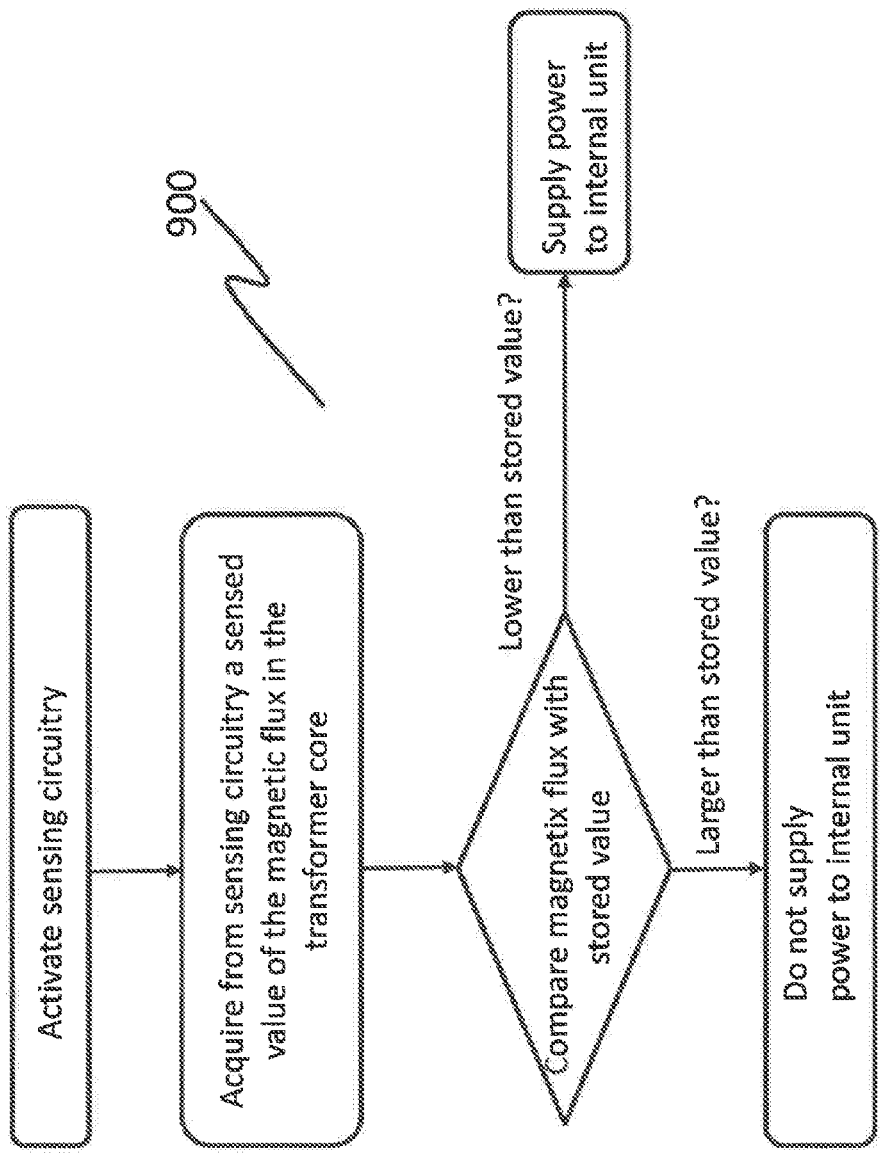

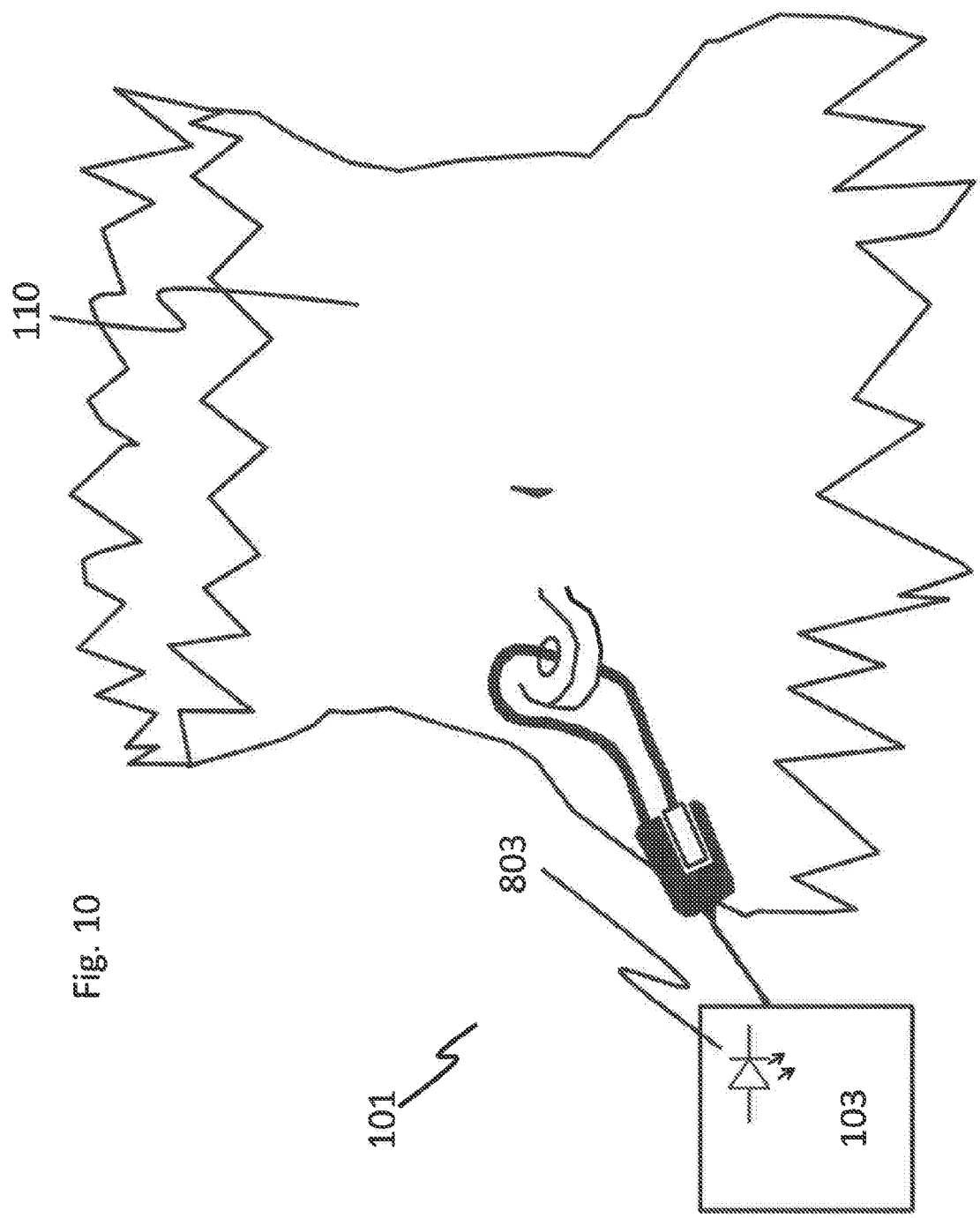

MEDICAL SYSTEM WITH CONNECTOR FORMING AN EXTERNAL WINDING

CROSS-REFERENCE TO RELATED APPLICATION

This Application is a Section 371 National Stage Application of International Application No. PCT/SE2020/051039, filed Oct. 27, 2020, which claims priority to Swedish Patent Application No. 1951275-5 filed on Nov. 7, 2019, and published as WO 2021/091454 A1 on May 14, 2021, in English, the entire contents of which are hereby incorporated by reference in their entireties.

FIELD OF THE INVENTION

The present invention relates to a medical system.

BACKGROUND OF THE INVENTION

Medical devices having one or more implantable units, generally referred to as implantable medical devices, have provided a wide range of benefits to patients over recent decades. In particular, devices such as implantable hearing aids, implantable pacemakers, defibrillators, eye implants, retina implants, heart pumps, ventricular assist devices, total artificial hearts, drug delivery systems, gastric implant, nerve stimulators, brain stimulators, functional electrical stimulation devices, such as cochlear prostheses, organ assist or replacement devices, and other partially or completely-implanted medical devices, have been successful in performing life-saving and/or lifestyle enhancement functions for a number of years.

As such, the type of implantable devices and the range of functions performed thereby have increased over the years. For example, many such implantable medical devices often include one or more instruments, apparatus, sensors, processors, controllers or other functional mechanical, electrical or electronic components that are permanently or temporarily implanted in a patient to perform diagnosis, prevention, monitoring, treatment or management of a disease or injury or symptom thereof, or to investigate, replace or modify of the anatomy or of a physiological process. Many of these implantable components receive power and/or receive data and/or transmit data over a wireless transcutaneous link from and/or to external units that are part of, or operate in conjunction with, the implantable unit.

The wireless transcutaneous link is conventionally realized as an inductive link, with an external unit comprising a transmitter winding and an implantable unit comprising a receiver winding. Typically, the receiver winding is implanted below the skin, and the transmitter winding is attached to the patient skin opposite to the implanted receiver winding such that the two windings are in parallel planes on both sides (external and implantable positions) of the skin. These systems are typically referred as TET links (TET—Transcutaneous Energy Transfer). For TET links it is rather difficult to fixate and position the transmitter winding to the skin of a patient. Gluing solutions and special vests to fixate/position the transmitter winding have been tried. Especially for life sustaining applications like heart pumps, ventricular assist devices or total artificial hearts this fixation/positioning is very critical. If the transmitter winding falls off or if it is in the wrong position the transcutaneous power transfer is affected and could in worst case be life threatening for the patient.

Further, for a conventional winding arrangement like the TET links where the transmitter winding and the receiver winding are on opposite sides of the skin and in parallel planes, the coupling coefficient is very low because most of the magnetic field lines that the transmitter winding generates are not picked up by the receiver winding, thus leading to poor energy transfer efficiency. In addition, as the two windings are located on opposite sides of the skin, any change in winding separation, for example by way of increase in skin thickness, may result in a rapid drop in the coupling coefficient between the two windings. In view of the efficiency problem, the external unit usually includes a relatively large battery compartment or multiple batteries so that the implantable medical device is useable for a usage period that doesn't cause annoyance for the user, for example requiring the user to frequently change or recharge the batteries. Further, also when the power efficiency is low it results in major energy losses in the transmitter winding and/or receiver winding which becomes hot. For life sustaining applications like heart pumps and total artificial hearts where the TET link runs in a continuous mode, this dissipated heat will result in skin heating. If this skin heating is too much it will result in skin necrosis i.e. the skin cells will die.

So-called skin tunnel transformers have been around to address these fixations, positioning and heating problems. Skin tunnel transformers as described in "IEEE TRANSACTIONS ON BIO-MEDICAL ENGINEERING, VOL. BME-15, NO. 4, OCTOBER 1968". The skin tunnel transformer has the advantage of a very high energy power transfer efficiency and a good positioning/fixation mechanism for life sustaining medical implants. However, to create the skin tunnel transformer one needs to either cut the transformer core in two parts to be able to mount it through the skin tunnel which will have a detrimental effect on the energy transfer efficiency or one need to feed the transmitter winding wire several times through the skin tunnel to achieve the optimum energy power transfer efficiency which is extremely non-user friendly. For life sustaining medical devices, like heart pumps or similar, feeding the transmitter winding wire several times through the skin tunnel is unacceptable from a safety point of view. If the number of turns of the winding are made to few or to many or made in the wrong direction the patient could die.

In view of the above, it would thus be desirable to provide for an improved medical system, especially to provide for an improved energy transfer between an external unit and an internal unit and to provide a safe and foolproof way to create the external second winding.

SUMMARY

It is an object of the present invention to provide for an improved medical system, especially to provide for an improved energy transfer between an external unit and an internal unit and to provide a safe and foolproof way to create the external second winding.

According to the present invention, it is therefore provided a medical system comprising an internal unit for implantation into a body of a patient; a transformer core to be arranged under the skin of the patient; internal cabling connecting the internal unit and the transformer core, the internal cabling comprising an internal winding around the transformer core; and an external unit to be outside the body of the patient, the external unit comprising power supply circuitry and external cabling coupled to the power supply circuitry for enabling supply of power from the power supply circuitry to the internal unit via the transformer core, wherein the external cabling comprises: a connector including a first connector part and a second connector part; a first conductive current path between the power supply circuitry and the first connector part, conductively connecting the first connector part and the power supply circuitry; a second conductive current path between the power supply circuitry and the second connector part, conductively connecting the second connector part and the power supply circuitry; and a third conductive current path between the first connector part and the second connector part, conductively connecting the first connector part and the second connector part, wherein the first connector part and the second connector part are joinable to conductively connect the first conductive current path to the second conductive current path via the third conductive current path so that a second winding can be formed around the transformer core by joining the first connector part and the second connector part.

The invention enables simple and secure formation of the second winding around an implanted transformer core with a hole pierced through the skin. One of the first and second connector parts can be passed through a healed pierced hole of the body of the patient, and thus through the transformer core once, and formation of the second winding can be achieved by joining the first connector part and the second connector part. This reduces the time for connecting the internal unit to the external unit at surgery and reduces the risk of formation of a faulty or unreliable connection of the second winding by removing potential sources of human error.

In one embodiment the internal unit comprises one or more of processing unit, rechargeable battery, vibrator, vibratory unit, electrode array, pump, sensor, drug, heart pump, ventricular asst device, total artificial heart.

The internal unit thus may be selected from a group consisting of one or more of:

i) an implantable hearing aid comprising a cochlear implant comprising an implantable electrode array configured to be positioned within a cochlea of the user, the electrode array being configured to deliver electrical charges in accordance with the output, ii) an implantable hearing aid comprising an auditory trans modal implant comprising an implantable electrode array configured to be positioned within a modiolus of the user, the electrode array being configured to deliver electrical charges in accordance with the output, iii) an implantable hearing aid comprising an auditory brainstem implant comprising an implantable electrode array (typically provided as a pad) configured to be implanted directly onto brainstem, the electrode array being configured to deliver the electrical charges in accordance with the output, iv) an implantable hearing aid comprising a bone conduction hearing aid comprising an implantable vibrator configured to be attached to skull of the user, the vibrator being configured to generate vibrations in accordance with the output, v) an implantable hearing aid comprising a middle ear implant comprising a vibratory unit configured to attach to one of the bones of the middle ear and/or to one of the windows of the cochlea, the vibratory unit being configured to generate vibrations in accordance with the output, vi) an artificial pacemaker comprising an electrode array configured to deliver electrical charges in accordance with the output.

vii) an implantable heart pump such as an impeller, a ventricular assist device (VAD) or a total artificial heart (TAH) comprising a pump configured to be attached to a user's heart, the pump being configured to provide blood flow within user's body, and vii) an implantable drug delivery system comprising an implantable capsule comprising a drug and a pump that is configured to attach to the implantable capsule and release, through a pumping action, a predefined amount of drug from the capsule to the user's body. In this embodiment, the drug delivery system may further include an implantable sensor that is configured to capture a biological data such as blood glucose level. The implantable processing unit is configured to receive the biological data and compare the received data with a stored normal range to determine a difference and accordingly, based on the difference, determine the amount of drug (predefined amount) to be released. The normal range, along with difference to amount of releasable drug may be stored as a look up table in a memory that the processing unit is configured to access. The processing unit is further configured, based on the determined predefined amount, to activate the pump (adapted to operationally connect to the capsule) for a duration that lets the predefined amount of the drug to be released from the capsule, viii) implantable deep brain stimulators or implantable nerve stimulators comprising an implantable electrode array configured to be implanted directly or indirectly onto the brain or nerve respectively, the electrode array being configured to deliver the electrical charges in accordance with the output comprising a stimulation pulse. The delivered electrical charges may be utilized to provide brain with information, viii) eye implants or retina implants comprising a camera for capturing images and an implantable electrode array configured to deliver electrical charges in accordance with the captured images, ix) an implantable cardioverter defibrillator comprising an electrode array (usually as electrical pads) configured to deliver electrical charges (for example by way of electrical shock) in accordance with a comparison of monitored rate and rhythm of the heart with a preset number. In this embodiment, the defibrillator may also include sensors in order to monitor the rate and rhythm of the heart, x) an implantable gastric stimulator configured to be implanted in an abdomen of the user and comprising an electrode array that is configured to deliver electrical charges (typically by way of mild electrical pulses) to nerves and smooth muscle of lower stomach of the user, and xi) an implantable brain computer interface system comprising an implantable sensor adapted to capture neural signals in response to brain activity.

xii) an implantable battery.

One or more of the above paragraphs refers to use of a medical device or a combination thereof. For example, a cochlear implant may be used alone but may also be used in combination such as providing mechanical stimulation by way of bone conduction hearing aid at a first ear and an electrical stimulation by way of cochlear implant at a second ear of the user. In another example, the same user may be utilizing a cochlear implant as well as an implantable cardioverter defibrillator. Other such examples of combinations are within the scope of embodiments of the invention.

In an embodiment the transformer core is preferably a solid continuous loop that is made up of a magnetic, like ferrite, material preferably having a high magnetic permeability. Such high magnetic permeability is at least 10, preferably at least 100, more preferably at least 1000. Such material may be selected from a group consisting of a ferrite material, and soft iron. Other commercially available products under brand names VACOFLUXT™, VACODUR™, VOCADUR S PLUS™, TRAFOPERM™, CRYOPERM™, PERMAX™, PERMENORM™, ULTRAPERM™, VACOPERM™, CHRONOPERM™, MEGAPERM™, MUMETALL™, RECOVAC™, and THERMOFLUX™, as produced by Vacuumschmelze GmbH & Co. KG or REMKO™ as produced by Uddeholm A/S may also be used. As the transformer core is made up of a material having a high magnetic permeability, most of the flux lines are concentrated within the magnetic material and thus allow for a high coupling coefficient between the second winding and the internal winding. It would be apparent to the skilled person that a material of different magnetic permeability may also be used so long as the material has high enough magnetic permeability to guide the flux lines generated in response to excitation of the second winding in a focused way towards the internal winding in a way explained in embodiments of the invention.

In an embodiment, the transformer core solid continuous loop is defined by a geometrical shape that includes a closed curve, defining a closed loop structure, wherein a point moving along the closed curve forms a path from a starting point to a final point that coincides with the starting point when the closed curve is in a closed mode.

In different embodiments, the transformer core solid continuous loop may include shape that is selected from a circular, elliptical, rectangular, square, polygonal shape, curved shape or a combination thereof.

In different embodiments the transformer core is a semi continuous loop with one or more narrow airgap(s).

In an embodiment the internal winding is formed by a conductive wire being wound around and along at least a part of the length of the transformer core. The number of turns of the winding could be 1-200 more preferably 1-50, and most preferably 1-20.

In an embodiment, the connector is selected from a group consisting of a connector clamp mechanism, connector spring mechanism, connector pin mechanism, connector snap-coupling mechanism between the first connector part and the second connector part, a connector magnetic coupling mechanism between the first connector part and the second connector part, and a combination thereof. As an example, one commercial connector used for implantable medical devices is Sygnus® from BalSeal®. Any other connector could also be used that is obvious for the person skilled in the art like Pogo pins, crown spring connector, pin socket connector etc.

In an embodiment, the connector has a locking function to avoid that the first connector part releases from the second connector part. In this embodiment the locking function is operated by the user i.e. the user can unlock the connector in order to open it or lock it after the connector has been closed in order to make it safe from accidentally opening the connector.

In an embodiment, the connector has a locking function to avoid that the first connector part releases from the second connector part. In this embodiment the locking function is non reversable i.e. when the connector is closed it is not possible to open it again.

In an embodiment, the external cabling is configured to form the second winding through a healed pierced hole of the body such that the transformer core and the second winding are arranged in an interlocked first hopf link configuration, and the transformer core and the internal winding are arranged in an interlocked second hopf link configuration. Because of the first hopf link configuration and second hopf link configuration, a substantial number of magnetic field lines are concentrated within the transformer core and passes through the internal winding, thereby substantially improving the coupling coefficient and the energy efficiency of the system. Further none of the second winding, the transformer core or the internal winding penetrates the human body outer skin surface.

In embodiments where the medical system includes an implantable heart pump, the internal unit may include a rechargeable battery. The external unit includes a power source that is adapted to excite the second winding and transfer power over the wireless transcutaneous energy link from the external unit to the internal unit. The internal unit is adapted to receive the power and the received power is used to charge the rechargeable battery, which is adapted to provide operational power to at least one of the components of internal unit. The internal unit may further include, as disclosed earlier, a heart pump, a ventricular assist device or a total artificial heart. The internal unit is adapted to utilize the power received from the rechargeable battery and process the electrical signal to compensate for heart circulation failure of the user, thus generating circulatory support (output) or complete circulatory support for the case where the heart is completely replaced by a total artificial heart. Depending upon the heart pump type, the circulatory support is delivered to part of the heart or to the complete heart.

In an embodiment of the medical system comprises a first connector part comprising a first locking member; a second connector part comprising a second locking member; and the first locking member and the second locking member are configured to interact with each other to lock the first connector part and the second connector part together when the first connector part and the second connector part are joined. Especially for critical medical applications a locking mechanism can prevent the first connector part to be unintentionally released from the second connector part resulting in severe medical consequences for the patient.

In an embodiment of the medical system, the connector locking mechanism is composed of the first locking member comprising an elastically deformable projection, and the second locking member comprising a recess dimensioned to receive the elastically deformable projection. Several other well-known locking mechanisms could also be used like screw locking mechanism, bayonet-screw locking mechanism, external key locking mechanism etc.

In an embodiment of the medical system the external unit further comprises sensing circuitry coupled to the external cabling and configured to sense a magnetic flux in the transformer core when the external cabling forms the second winding around the transformer core. By time multiplexing the connection of the external second winding it is possible to measure the induced voltage in the external second winding and to calculate the magnetic flux in the transformer core according to principle of Faraday's law. Further it is possible, using process circuitry in the external unit, to control the power supply circuitry to supply power to the internal unit via the transformer core when the magnetic flux in the transformer core is lower than a predetermined value.

In an embodiment of the medical system the external unit further comprises an indicator when power is being provided by the external unit to the internal unit. The indicator could be visual for example an LED or a sound or a tactile indication.

In summary, the present invention thus relates to a medical system comprising an internal unit; a transformer core; internal cabling connecting the internal unit and the transformer core, the internal cabling comprising an internal winding around the transformer core; and an external unit comprising power supply circuitry and external cabling coupled to the power supply circuitry for enabling supply of power from the power supply circuitry to the internal unit via the transformer core. The external cabling comprises a connector including a first connector part and a second connector part; a first conductive current path between the power supply circuitry and the first connector part, conductively connecting the first connector part and the power supply circuitry; a second conductive current path between the power supply circuitry and the second connector part, conductively connecting the second connector part and the power supply circuitry; and a third conductive current path between the first connector part and the second connector part, conductively connecting the first connector part and the second connector part.

BRIEF DESCRIPTION OF THE DRAWINGS

These and other aspects of the present invention will now be described in more detail, with reference to the appended drawings showing an example embodiment of the invention, wherein:

FIG. 3A illustrates a medical system with a first and a second connector part in an opened state, according to an embodiment of the invention;

FIG. 3B illustrates a medical system with a first and a second connector part in a joined state, according to an embodiment of the invention;

FIG. 4A illustrates a conventional winding having two turns;

FIG. 4B illustrates a second winding with a first and a second connector part in an opened state, according to an embodiment of the invention;

FIG. 4C illustrates a second winding having two turns with a first and a second connector part in a joined state, according to an embodiment of the invention;

FIG. 5A illustrates a conventional winding having three turns;

FIG. 5B illustrates a second winding with a first and a second connector part in an opened state, according to an embodiment of the invention;

FIG. 5C illustrates a second winding having three turns with a first and a second connector part in a joined state, according to an embodiment of the invention;

FIG. 6A illustrates the connector in a non-locked open state with the first connector part comprising a first locking member and the second connector part comprising a second locking member according to an embodiment of the invention;

FIG. 6B illustrates the connector in a locked joined state with the first connector part comprising a first locking member and the second connector part comprising a second locking member according to an embodiment of the invention;

FIG. 7A illustrates the external unit of a medical system with an opened connector, according to an embodiment of the invention;

FIG. 8 illustrates the external unit of a medical system with sensing circuitry configured to sense a magnetic flux in the transformer core, according to an embodiment of the invention;

FIG. 9 illustrates the flowchart of the processing circuitry configured to activate the sensing circuitry according to an embodiment of the invention; and FIG. 10 illustrates the indicator of the external unit of a medical system according to an embodiment of the invention.

DETAILED DESCRIPTION OF EXAMPLE EMBODIMENTS

In the present detailed description, various embodiments of the method, external unit and medical system according to the present invention are mainly described with reference to a heart pump system. It should be noted that this by no means limits the scope of the present invention as defined by the claims, which also encompass, for instance, implantable hearing aids, implantable pacemakers, defibrillators, eye implants, retina implants, heart pumps, ventricular assist devices, total artificial hearts, drug delivery systems, gastric implant, nerve stimulators, brain stimulators, functional electrical stimulation devices, such as cochlear prostheses, organ assist or replacement devices, and other partially or completely-implanted medical devices.

Figure 1:
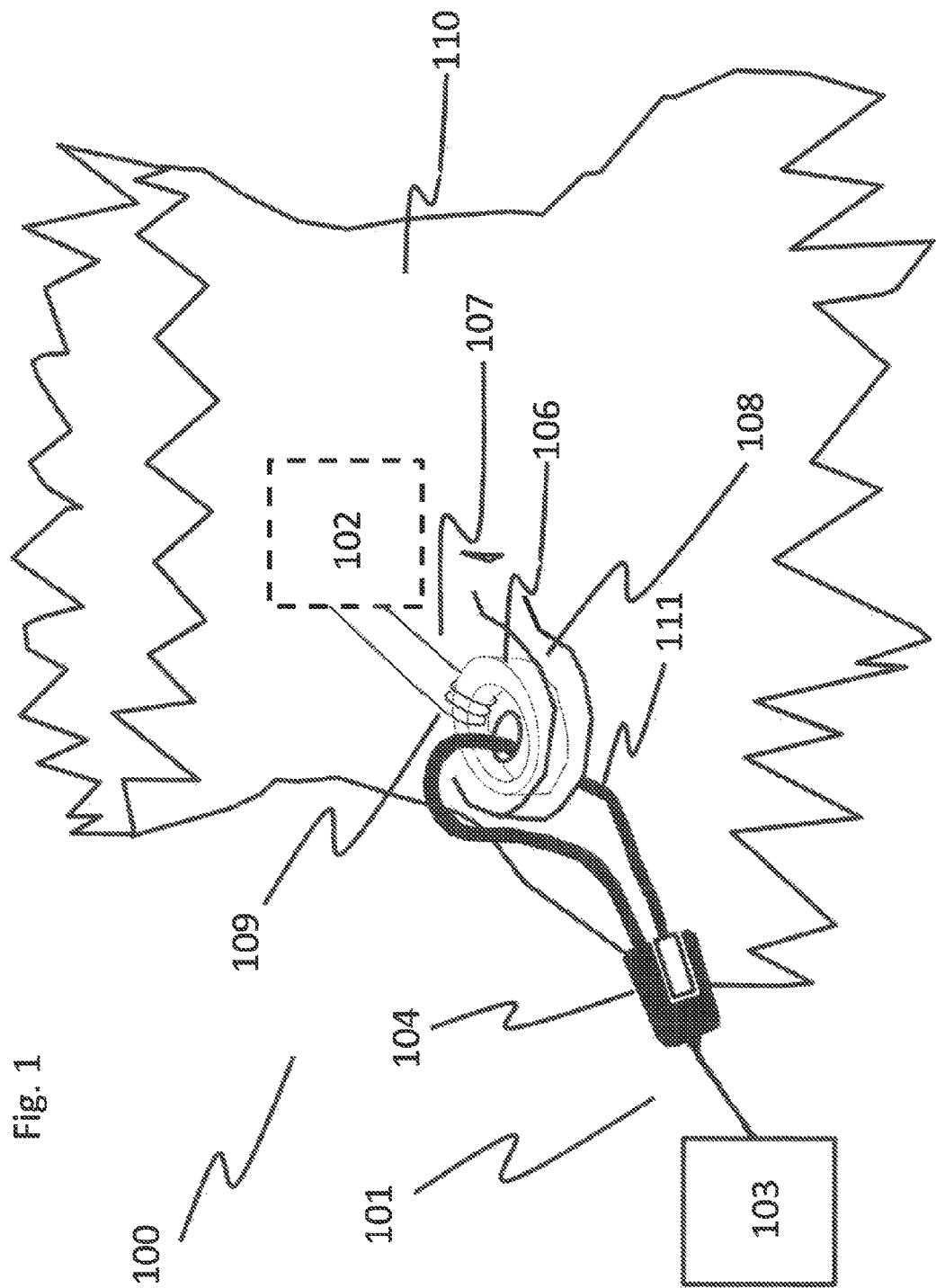
FIG. 1 illustrates a medical system with connector forming a second winding according to an embodiment of the invention.

FIG. 1 illustrates a medical system 100 with a connector 104 forming a second winding 111 according to an embodiment of the invention. The medical system 100 comprises of an internal unit 102 for implantation into a body 110 of a patient, a transformer core 106 to be arranged under the skin 108 of the patient, an internal cabling 107 connecting the internal unit 102 and the transformer core 106, the internal cabling comprises an internal winding 109 around the transformer core 106 and an external unit 101 to be outside the body of the patient, the external unit 101 comprising a power supply circuitry 103 and external cabling coupled to the power supply circuitry 103 for enabling supply of power from the power supply circuitry to the internal unit 102 via the transformer core 106.

Figure 2:
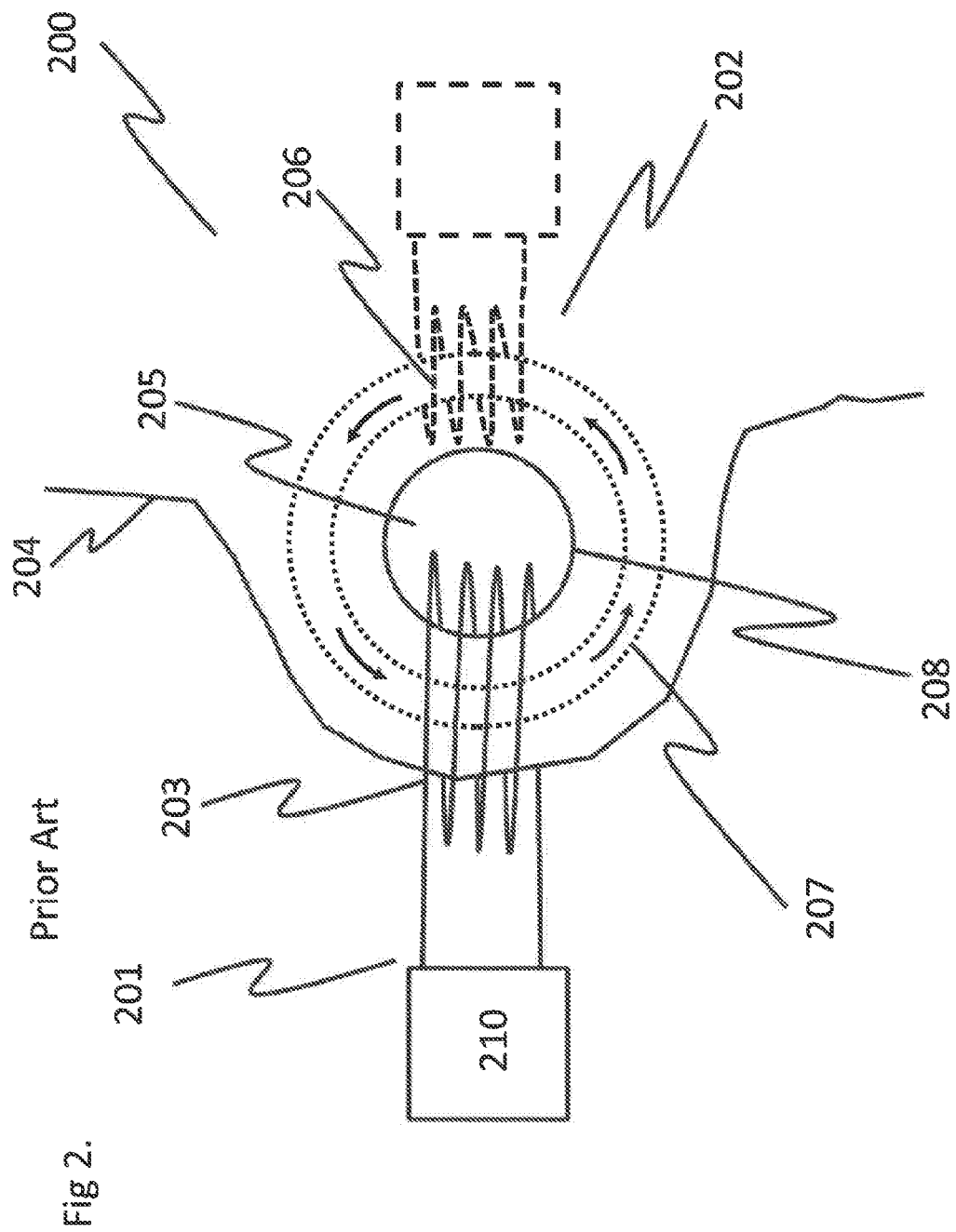
FIG. 2 illustrates prior art of a medical system comprising a wireless transcutaneous energy link.

FIG. 2 illustrates a prior art implantable medical device 200 comprising a wireless transcutaneous link. The medical device 200 includes an external unit 201 and an internal unit 202. The external unit 201 comprises power supply circuitry 210 and external cabling 203 coupled to the power supply circuitry for enabling supply of power from the power supply circuitry to the internal unit 202 via the transformer core 207. The external cabling 203 is being wound around the transformer core 207 through a pierced opening 205 in the skin 204. The internal unit 202 includes a transformer 207 core and internal cabling connecting the internal unit and the transformer core, the internal cabling comprising an internal winding 206 around the transformer core 207. However, the winding of the external cabling 203 around the transformer core 207 through the pierced skin opening 205 creates several problems. For medical devices it is necessary to design the medical device in a way, so it is not possible to mount the device in a wrong way. Even with very detailed instructions of how the windings of the external cabling 203 should be made (for examples number of turns of the winding and winding direction) it is not safe enough especially for life sustaining medical devices like heart pumps. Secondly it is will become very tight with several windings in the pierced opening 205 of the skin since each winding needs to have its own protective wearing and insulated layer.

FIGS. 3A and 3B illustrate a medical system 100 according to an embodiment of the invention. The medical system 100 comprises of an internal unit 102 for implantation into a body 110 of a patient, a transformer core 106 to be arranged under the skin 108 of the patient, an internal cabling 107 connecting the internal unit 102 and the transformer core 106, the internal cabling comprises an internal winding 109 around the transformer core 106 and an external unit 101 to be outside the body of the patient, the external unit 101 comprising power supply circuitry 103 and external cabling 301 coupled to the power supply circuitry 103 for enabling supply of power from the power supply circuitry to the internal unit 102 via the transformer core 106. The external cabling 301 comprises a connector including a first connector part 302 and a second connector part 303, a first conductive current path 304 between the power supply circuitry 103 and the first connector part 302, conductively connecting the first connector part 302 and the power supply circuitry 103, a second conductive current path 305 between the power supply circuitry 103 and the second connector part 303, conductively connecting the second connector part 303 and the power supply circuitry 103 and a third conductive current path 306 between the first connector part 302 and the second connector part 303, conductively connecting the first connector 302 part and the second connector part 303, wherein the first connector part 302 and the second connector part 303 are joinable to conductively connect the first conductive current path 304 to the second conductive current path 305 via the third conductive current path 306 so that a second winding can be formed around the transformer core 106 by joining the first connector part 302 and the second connector part 303. FIG. 3A shows when the first connector part 302 and the second connector part 303 are not connected. FIG. 3B shows when the first connector part 302 and the second connector part 303 are connected. Further in FIG. 3B activating an ac-voltage of the power supply circuitry 103 connected to the second winding formed around the transformer core 106 a time varying magnetic flux 120 is formed in the transformer core 106 transferring energy to the internal unit 102 via the internal winding. In the embodiment the internal unit 102 is an implantable heart pump such as an impeller, a ventricular assist device (VAD) or a total artificial heart (TAH) comprising a pump configured to be attached to a user's heart, the pump being configured to provide blood flow within user's body.

FIG. 4A illustrates a traditional winding 400 composed of two turns.

FIG. 4B illustrates the external cabling 301 according to an embodiment of the invention. The external cabling 301 comprises a connector including a first connector part 302 and a second connector part 303, a first conductive current path 304, a second conductive current path 305 and a third conductive current path 306 between the first connector part 302 and the second connector part 303, conductively connecting the first connector 302 part and the second connector part 303, wherein the first connector part 302 and the second connector part 303 are joinable to conductively connect the first conductive current path 304 to the second conductive current path 305 via the third conductive current path 306 so that a second winding can be formed by joining the first connector part 302 and the second connector part 303. FIG. 4B shows when the first connector part 302 and the second connector part 303 are not connected. FIG. 4C shows when the first connector part 302 and the second connector part 303 are connected. In more detail the first conductive current path 304 connects Y to A1. The second conductive current path 305 connects X to B2. The third conductive current path 306 connects B1 to A2. By joining the first connector part 302 and the second connector part 303, as in FIG. 4C A1 is connected to A2 and B1 is connected to B2 which means that a winding is created with same number of turns as the winding 400 shown in FIG. 4A.

FIG. 5A illustrates a traditional winding 500 composed of three turns.

FIG. 5B illustrates the external cabling according to an embodiment of the invention. The external cabling 301 comprises a connector including a first connector part 302 and a second connector part 303, a first conductive current path 304, a second conductive current path 305, a third conductive current path 306 between the first connector part 302 and the second connector part 303 and a fourth conductive current path 307 between the first connector part 302 and the second connector part 303, conductively connecting the first connector 302 part and the second connector part 303, wherein the first connector part 302 and the second connector part 303 are joinable to conductively connect the first conductive current path 304 to the second conductive current path 305 via the third conductive current path 306 and the fourth conductive current path 307 in series so that the second winding can be formed by joining the first connector part 302 and the second connector part 303.

FIG. 5B shows when the first connector part 302 and the second connector part 303 are not connected. FIG. 5C shows when the first connector part 302 and the second connector part 303 are connected. In more detail the first conductive current path 304 connects Y to A1. The second conductive current path 305 connects X to C2. The third conductive current path 306 connects C1 to B2. The fourth conductive current path 307 connects B1 to A2. By joining the first connector part 302 and the second connector part 303, as illustrated in FIG. 5C, A1 is connected to A2, B1 is connected to B2 and C1 is connected to C2 which means that a winding is created with same number of turns as the winding 500 shown in FIG. 5A.

FIG. 6A Illustrates the connector 104 in a non-locked open state with the first connector part 302 comprising a first locking member and the second connector part 303 comprising a second locking member according to an embodiment of the invention.

FIG. 6B illustrates the connector in a locked joined state with the first connector part 302 comprising a first locking member and the second connector part 303 comprising a second locking member according to an embodiment of the invention, wherein the first locking member comprises an elastically deformable projection 602 and 603, and the second locking member comprises a recess 601 dimensioned to receive the elastically deformable projection.

FIG. 7A illustrates the external unit with an opened connector, according to an embodiment of the invention. It illustrates the external unit just prior to that the second connector part 303 is pushed through the pierced skin opening 205 of the human body 110.

Figure 7B:
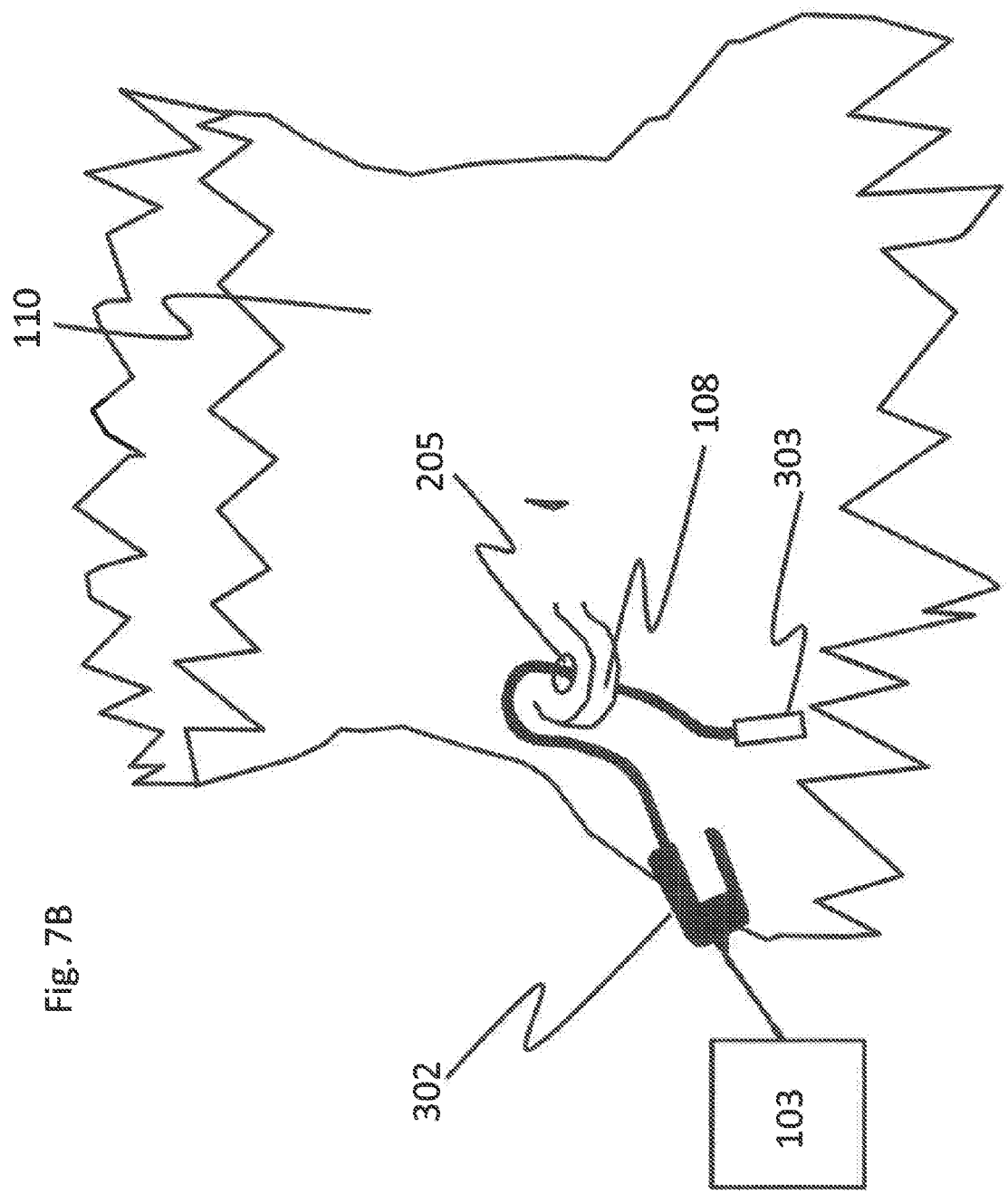
FIG. 7B illustrates the external unit of a medical system with an opened connector where part of the external cabling is inserted in a pierced opening of a human body, according to an embodiment of the invention.

FIG. 7B illustrates the external unit with an opened connector, according to an embodiment of the invention. It illustrates the external unit just after that the second connector part 303 is pushed through the pierced skin opening 205 of the human body 110.

Figure 7C:
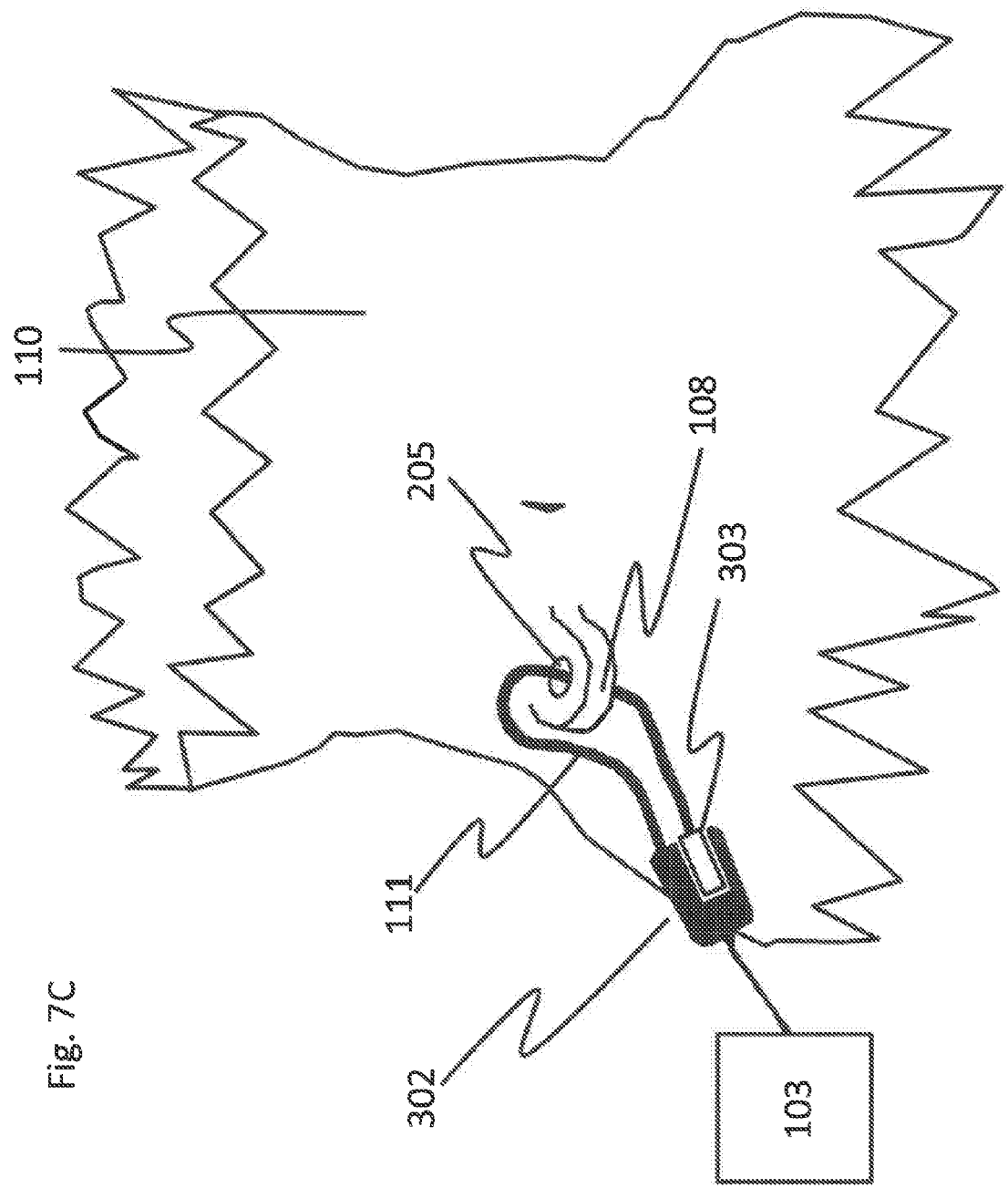
FIG. 7C illustrates the external unit of a medical system with a joined connector, according to an embodiment of the invention.

FIG. 7C illustrates the external unit with a joined closed connector, according to an embodiment of the invention. It illustrates how the second connector part 303 has been joined to the first connector part 302 just after it has been pushed through the pierced skin opening 205 of the human body 110.

FIG. 8 illustrates the external unit of a medical system 100 with sensing circuitry configured to sense a magnetic flux in the transformer core, according to an embodiment of the invention. By using time multiplexing control, the power circuitry 103 is disconnected from the external cabling using disconnection means 801, it is possible to use the sensing circuitry 800 connected to the external cabling 301 to measure the induced voltage caused by the time varying magnetic flux 802 in the transformer core 106, using the principle of Faraday's law.

FIG. 9 illustrates the flowchart 900 of the processing circuitry configured to activate the sensing circuitry according to an embodiment of the invention. The sensing circuitry is activated to sense the magnetic flux in the transformer core. The sensing circuitry returns a sensed value related to the amount of magnetic flux in the transformer core. The sensed value is then compared with a stored value indicative of the threshold magnetic flux. If the sensed value is lower than the stored value the power supply circuitry is activated to supply power to the internal unit via the transformer core.

FIG. 10 illustrates the indicator of external unit 101 of a medical system according to an embodiment of the invention. The external unit 101 comprises a LED indicator 803 for providing an indication to an operator or the patient when power is being provided by the external unit to the internal unit.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A medical system comprising:
an internal unit for implantation into a body of a patient;
a transformer core to be arranged under a skin of the patient;
internal cabling connecting the internal unit and the transformer core, the internal cabling comprising an internal winding around the transformer core; and
an external unit to be outside the body of the patient, the external unit comprising power supply circuitry and external cabling coupled to the power supply circuitry for enabling supply of power from the power supply circuitry to the internal unit via the transformer core,
wherein the external cabling comprises:
a connector including a first connector part and a second connector part;
a first conductive current path between the power supply circuitry and the first connector part, conductively connecting the first connector part and the power supply circuitry;
a second conductive current path between the power supply circuitry and the second connector part, conductively connecting the second connector part and the power supply circuitry; and
a third conductive current path between the first connector part and the second connector part, conductively connecting the first connector part and the second connector part,
wherein the external cabling is configured in such a way that passing the second connector part through the transformer core once results in the second conductive current path and the third conductive current path simultaneously passing through the transformer core,
wherein the first connector part and the second connector part are joinable to conductively connect the first conductive current path to the second conductive current path via the third conductive current path so that a second winding can be formed around the transformer core by joining the first connector part and the second connector part.

2. The medical system according to claim 1, wherein the external cabling further comprises a fourth conductive current path between the first connector part and the second connector part, conductively connecting the first connector part and the second connector part,
wherein the first connector part and the second connector part are joinable to conductively connect the first conductive current path to the second conductive current path via the third conductive current path and the fourth conductive current path in series so that the second winding can be formed around the transformer core by joining the first connector part and the second connector part.

3. The medical system according to claim 1, wherein:
the first connector part comprises a first locking member;
the second connector part comprises a second locking member; and
the first locking member and the second locking member are configured to interact with each other to lock the first connector part and the second connector part together when the first connector part and the second connector part are joined.

4. The medical system according to claim 3, wherein the first locking member comprises an elastically deformable projection, and the second locking member comprises a recess dimensioned to receive the elastically deformable projection.

5. The medical system according to claim 1, wherein the external unit further comprises sensing circuitry coupled to the external cabling and configured to sense a magnetic flux in the transformer core when the external cabling forms the second winding around the transformer core.

6. The medical system according to claim 5, wherein the external unit further comprises processing circuitry configured to:
activate the sensing circuitry;
acquire, from the sensing circuitry, a signal indicative of a sensed value indicating the magnetic flux in the transformer core;
compare the sensed value with a stored value indicative of a threshold magnetic flux; and
control the power supply circuitry to supply power to the internal unit via the transformer core when the comparison indicates that the magnetic flux in the transformer core is lower than the threshold magnetic flux.

7. The medical system according to claim 6, wherein:
the external unit further comprises an indicator for providing an indication to an operator; and the processing circuitry is further configured to control the indicator to provide a predefined indication when power is being provided by the external unit to the internal unit.

8. The medical system according to claim 1, wherein the internal unit comprises one or more of a cochlear implant, an auditory transmodiolar implant, an auditory brainstem implant, a bone conduction hearing aid, a middle ear implant, an artificial pacemaker, a ventricular assist device (VAD), a total artificial heart, an eye implant or retina implant, a nerve stimulator, a deep brain stimulator, a drug delivery system, a brain computer interface system, a cardioverter defibrillator, a gastric stimulator, a brain computer interface system or a rechargeable battery.

* * * * *